(12) United States Patent
Adams et al.

(10) Patent No.: US 6,365,598 B1
(45) Date of Patent: Apr. 2, 2002

(54) PYRROLOQUINOLINES FOR TREATMENT OF OBESITY

(75) Inventors: David Reginald Adams; Jonathan Mark Bentley; Jonathan Richard Anthony Roffey; Corinna Dagmar Bodkin; Howard Langham Mansell; Ashley Roger George; Ian Anthony Cliffe, all of Wokingham (GB)

(73) Assignee: Vernalis Research Limited, Wokingham (GB)

( * ) Notice: Subject to any disclaimer, the term of this patent is extended or adjusted under 35 U.S.C. 154(b) by 0 days.

(21) Appl. No.: 09/786,159

(22) PCT Filed: Sep. 1, 1999

(86) PCT No.: PCT/GB99/02887

§ 371 Date: Mar. 1, 2001

§ 102(e) Date: Mar. 1, 2001

(87) PCT Pub. No.: WO00/12502

PCT Pub. Date: Mar. 9, 2000

(30) Foreign Application Priority Data

Sep. 1, 1998 (GB) ............................................. 9819019

(51) Int. Cl.$^7$ ..................... A61K 31/437; C07D 47/104
(52) U.S. Cl. ......................... 514/292; 546/84; 544/179; 544/180; 544/234; 514/246; 514/248; 514/250
(58) Field of Search .................. 514/292, 246, 514/248, 250; 546/84; 544/179, 180, 234

(56) References Cited

FOREIGN PATENT DOCUMENTS

| EP | 0 655 440 | 5/1995 |
| EP | 0 657 426 | 6/1995 |
| EP | 0 700 905 | 3/1996 |
| WO | 98/30548 | 7/1998 |

OTHER PUBLICATIONS

G.A. Kennett, 5–HT$_{1C}$ Receptors and Their Therapeutic Relevance, Current Drugs LTD ISSN 0967–8298, 1983, pp. 317–362.

N. Upton, Studies on the Role of 5–HT$_{2C}$ and 5–HT$_{2B}$ Receptors in Regulating Generalised Seizure Threshold in Rodents, *European Journal of Pharmacology 359*, Oct. 1998, pp. 33–40.

G. Redmond, Mood Disorders in the Female Patient, *Int. Journal of Fertil. 42(2)*, 1997, pp. 67–72.

J. Valentine et al., Differential Involvement of Serotonin 2A/C and Thromboxane A$_2$/Prostanoid Receptors in High–vs. Low–Shear Rate Arterial Thrombosis in Rabbits, *The Journal of Pharmacology and Experimental Therapeutics*, 1997, pp. 761–769.

L. Kubin et al., Serotonergic Excitatory Drive to Hypoglossal Motoneurons in the Decerebrate Cat, *Neuroscience Letters*, 139, 1992, pp. 243–248.

*Primary Examiner*—C. S. Aulakh
(74) *Attorney, Agent, or Firm*—Foley & Lardner

(57) ABSTRACT

A chemical compound of formula (I), wherein $R_1$ to $R_3$ are independently selected from hydrogen and alkyl; $R_4$ is selected from hydrogen, alkyl, alkoxy, formyl and cyano; $X_1$ is selected from N and C—$R_7$; $X_2$ is selected from N and C—$R_8$; $X_3$ is selected from N and C—$R_9$; $X_4$ is selected from N and C—$R_{10}$; wherein at least one of $X_1$, $X_2$, $X_3$ and $X_4$ is N; and $R_5$ to $R_{10}$ are independently selected from hydrogen, halogen, hydroxy, alkyl, aryl, alkoxy, aryloxy, alkylthio, arylthio, alkylsulfoxyl, alkylsulfonyl, arylsulfoxyl, arylsulfonyl, amino, monoalkylamino, dialkylamino, nitro, cyano, carboxaldehyde, alkylcarbonyl, arylcarbonyl, aminocarbonyl, monoalkylaminocarbonyl, dialkylaminocarbonyl, alkoxycarbonylamino, aminocarbonyloxy, monoalkylaminocarbonyloxy, dialkylaminocarbonyloxy, monoalkylaminocarbonylamino and dialkylaminocarbonylamino, and the use thereof in therapy, particularly for the treatment of disorders of the central nervous system; damage to the central nervous system; cardiovascular disorders; gastrointestinal disorders; diabetes insipidus; and sleep apnea, and particularly for the treatment of obesity.

29 Claims, No Drawings

PYRROLOQUINOLINES FOR TREATMENT OF OBESITY

The present invention relates to pyrroloquinoline derivatives, to processes and intermediates for their preparation, to pharmaceutical compositions containing them and to their medicinal use. The active compounds of the present invention are useful in treating obesity and other disorders.

It has been recognised that obesity is a disease process influenced by environmental factors in which the traditional weight loss methods of dieting and exercise need to be supplemented by therapeutic products (S. Parker, "Obesity: Trends and Treatments", Scrip Reports, PJB Publications Ltd, 1996).

Whether someone is classified as overweight or obese is generally determined on the basis of their body mass index (BMI) which is calculated by dividing body weight (kg) by height squared (m$^2$). Thus, the units of BMI are kg/m$^2$ and it is possible to calculate the BMI range associated with minimum mortality in each decade of life. Overweight is defined as a BMI in the range 25–30 kg/m$^2$, and obesity as a BMI greater than 30 kg/m . There are problems with this definition in that it does not take into account the proportion of body mass that is muscle in relation to fat (adipose tissue). To account for this, obesity can also be defined on the basis of body fat content: greater than 25% and 30% in males and females, respectively.

As the BMI increases there is an increased risk of death from a variety of causes that is independent of other risk factors. The most common diseases with obesity are cardio-vascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Compounds marketed as anti-obesity agents include Orlistat (Reductil®) and Sibutramine. Orlistat (a lipase inhibitor) inhibits fat absorption directly and tends to produce a high incidence of unpleasant (though relatively harmless) side-effects such as diarrhoea. Sibutramine (a mixed 5-HT/noradrenaline reuptake inhibitor) can increase blood pressure and heart rate in some patients. The serotonin releaser/reuptake inhibitors fenfluramine (Pondimine®) and dexfenfluramine (Redux™) have been reported to decrease food intake and body weight over a prolonged period (greater than 6 months). However, both products were withdrawn after reports of preliminary evidence of heart valve abnormalities associated with their use. There is therefore a need for the development of a safer anti-obesity agent.

The non-selective 5-HT$_{2C}$ receptor agonists/partial agonists m-chlorophenylpiperazine (mCPP) and trifluoromethylphenylpiperazine (TFMPP) have been shown to reduce food intake in rats (G. A. Kennett and G. Curzon, Psychopharmacol., 1988, 96, 93–100; G. A. Kennett, C. T. Dourish and G. Curzon, Eur. J. Pharmacol., 1987, 141, 429–435) and to accelerate the appearance of the behavioural satiety sequence (S. J. Kitchener and C. T. Dourish, Psychopharmacol., 1994, 113, 369–377). Recent findings from studies with mCPP in normal human volunteers and obese subjects have also shown decreases in food intake. Thus, a single dose of mCPP decreased food intake in female volunteers (A. E. S. Walsh et al., Psychopharmacol., 1994, 116, 120–122) and decreased the appetite and body weight of obese male and female subjects during subchronic treatment for a 14 day period (P. A. Sargeant et al., Psychopharmacol., 1997, 133, 309–312). The anorectic action of mCPP is absent in 5-HT$_{2C}$ receptor knockout mutant mice (L. H. Tecott et al., Nature, 1995, 374, 542–546) and is antagonised by the 5-HT$_{2C}$ receptor antagonist SB-242084 in rats (G. A. Kennett et al., Neuropharmacol., 1997, 36, 609–620). It seems therefore that mCPP decreases food intake via an agonist action at the 5-HT$_{2C}$ receptor.

Other compounds which have been proposed as 5-HT$_{2C}$ receptor agonists for use in the treatment of obesity include the substituted 1-aminoethyl indoles disclosed in EP-A-0655440. CA-2132887 and CA-2153937 disclose that tri-cyclic I-aminoethylpyrrole derivatives and tricyclic 1-aminoethyl pyrazole derivatives bind to 5-HT$_{2C}$ receptors and may be used in the treatment of obesity. WO-A-98/30548 discloses aminoalkylindazole compounds as 5-HT$_{2C}$ agonists for the treatment of CNS diseases and appetite regulation disorders. WO-A-98/56768 discloses various tri-cyclic pyrrole and pyrazole derivatives having 5-HT$_{2c}$ receptor affinity and their use for the treatment of CNS diseases and appetite regulation disorders.

It is an object of this invention to provide selective, directly acting 5HT$_2$ receptor ligands for use in therapy and particularly for use as anti-obesity agents. It is a further object of this invention to provide directly acting ligands selective for 5-HT$_{2B}$ and/or 5-HT$_{2C}$ receptors, for use in therapy and particularly for use as anti-obesity agents. It is a further object of this invention to provide selective, directly acting 5-HT$_{2C}$ receptor ligands, preferably 5-HT$_{2C}$ receptor agonists, for use in therapy and particularly for use as anti-obesity agents.

According to the present invention there is provided a chemical compound of formula (I):

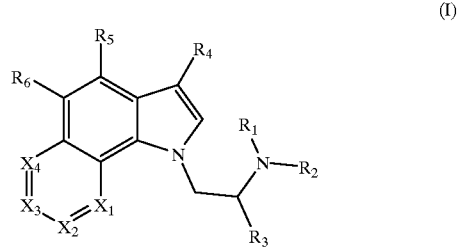

wherein:
R$_1$ to R$_3$ are independently selected from hydrogen and alkyl;
R$_4$ is selected from hydrogen, alkyl, alkoxy, cyano and formyl;
X$_1$ is selected from N and C—R$_7$;
X$_2$ is selected from N and C—R$_8$;
X$_3$ is selected from N and C—R$_9$;
X$_4$ is selected from N and C—R$_{10}$;
wherein at least one of X$_1$, X$_2$, X$_3$ and X$_4$ is N; and
R$_5$ to R$_{10}$ are independently selected from hydrogen, halogen, hydroxy, alkyl, aryl, alkoxy, aryloxy, alkylthio, arylthio, alkylsulfoxyl, alkylsulfonyl, arylsulfoxyl, arylsulfonyl, amino, monoalkylamino, dialkylamino, nitro, cyano, carboxaldehyde, alkylcarbonyl, arylcarbonyl, aminocarbonyl, monoalkylaminocarbonyl, dialkylaminocarbonyl, alkoxycarbonylamino, aminocarbonyloxy, monoalkylaminocarbonyloxy, dialkylaminocarbonyloxy, monoalkylaminocarbonylamino and dialkylaminocarbonylamino, and pharmaceutically acceptable salts and prodrugs thereof.

As used herein, the term "alkyl" means a branched or unbranched, cyclic or acyclic, saturated or unsaturated (e.g. alkenyl or alkynyl) hydrocarbyl radical. Where cyclic, the alkyl group is preferably $C_3$ to $C_{12}$, more preferably $C_5$ to $C_{10}$, more preferably $C_5$, $C_6$ or $C_7$. Where acyclic, the alkyl group is preferably $C_1$ to $C_{10}$, more preferably $C_1$ to $C_6$, more preferably methyl, ethyl, propyl (n-propyl or isopropyl) or butyl (n-butyl, isobutyl or tertiary-butyl), more preferably methyl.

As used herein, the term "lower alkyl" means methyl, ethyl, propyl (n-propyl or isopropyl) or butyl (n-butyl, isobutyl or tertiary-butyl).

As used herein, the term "aryl" means an aromatic group, such as phenyl or naphthyl, or a heteroaromatic group containing one or more, preferably one, heteratom, such as pyridyl, pyrrolyl, furanyl and thienyl.

The alkyl and aryl groups may be substituted or unsubstituted. Where substituted, there will generally be 1 to 3 substituents present, preferably 1 substituent. Substituents may include:

carbon-containing groups such as
   alkyl,
   aryl,
   arylalkyl (e.g. substituted and unsubstituted phenyl, substituted and unsubstituted benzyl);
halogen atoms and halogen-containing groups such as
   haloalkyl (e.g. trifluoromethyl);
oxygen-containing groups such as
   alcohols (e.g. hydroxy, hydroxyalkyl, aryl(hydroxy)alkyl),
   ethers (e.g. alkoxy, aryloxy, alkoxyalkyl, aryloxyalkyl),
   aldehydes (e.g. carboxaldehyde),
   ketones (e.g. alkylcarbonyl, alkylcarbonylalkyl, arylcarbonyl, arylalkylcarbonyl, arylcarbonylalkyl),
   acids (e.g. carboxy, carboxyalkyl),
   acid derivatives such as esters (e.g. alkoxycarbonyl, alkoxycarbonylalkyl, alkylcarbonyloxy, alkylcarbonyloxyalkyl),
   amides (e.g. aminocarbonyl, mono- or di-alkylaminocarbonyl, aminocarbonylalkyl, mono- or di-alkylaminocarbonylalkyl, arylaminocarbonyl),
   carbamates (e.g. alkoxycarbonylamino, aryloxycarbonylamino, aminocarbonyloxy, mono- or di-alkylaminocarbonyloxy, arylaminocarbonyloxy)
   and ureas (e.g. mono- or di-alkylaminocarbonylamino or arylaminocarbonylamino);
nitrogen-containing groups such as
   amines (e.g. amino, mono- or di-alkylamino, aminoalkyl, mono- or di-alkylaminoalkyl),
   azides,
   nitriles (e.g. cyano, cyanoalkyl),
   nitro;
sulfur-containing groups such as
   thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl);
and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazoidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

As used herein, the term "alkoxy" means alkyl-O— and "alkoyl" means alkyl-O—. Alkoxy substituent groups or alkoxy-containing substituent groups may be substituted by one or more alkyl groups.

As used herein, the term "halogen" means a fluorine, chlorine, bromine or iodine radical, preferably a fluorine, chlorine or bromine radical, and more preferably a fluorine or chlorine radical.

As used herein the term "prodrug" means any pharmaceutically acceptable prodrug of the compound of formula (I).

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, succinic, sulfuric and methanesulfonic acids. Acceptable base salts include alkali metal (e.g. sodium, potassium), alkaline earth metal (e.g. calcium, magnesium) and aluminium salts.

Preferably, the compounds of formula (I) are selected from compounds in which $R_1$ is the same as $R_2$. Preferably, $R_1$ and $R_2$ are both hydrogen.

In an embodiment of the invention, $R_1$ is hydrogen and $R_2$ is alkyl, preferably lower alkyl, preferably methyl. In a preferred embodiment, $R_1$ is hydrogen and $R_2$ is arylalkyl, preferably arylmethyl. Where $R_2$ is arylalkyl, it is preferred that said aryl substituent is a substituted or unsubstituted phenyl or thienyl group.

Preferably, the compounds of formula (I) are selected from compounds in which $R_3$ is alkyl, preferably lower alkyl, preferably methyl. Where $R_3$ is alkyl, the carbon atom to which $R_3$ is attached is an asymmetric carbon atom. It is preferred that this asymmetric carbon atom is in the (S)-configuration, wherein the stereochemical assignment is defined with respect to a compound wherein $R_3$ is an unsubstituted alkyl group.

$R_5$ to $R_{10}$ are independently selected from hydrogen, halogen, hydroxy, alkyl (including cycloalkyl, halo-alkyl (such as trifluoromethyl) and arylalkyl), aryl, alkoxy (including arylalkoxy), aryloxy, alkylthio, arylthio, alkylsulfoxyl, alkylsulfonyl, arylsulfoxyl, arylsulfonyl, amino, monoalkylamino, dialkylamino, nitro, cyano, carboxaldehyde, alkylcarbonyl, arylcarbonyl, aminocarbonyl, monoalkylaminocarbonyl, dialkylaminocarbonyl, alkoxycarbonylamino, aminocarbonyloxy, monoalkylaminocarbonylamino, dialkylaminocarbonyloxy, monoalkylaminocarbonylamino and dialkylaminocarbonylamino.

In one embodiment of the invention $R_5$ to $R_{10}$ are independently selected from hydrogen, halogen, hydroxy, alkyl (including cycloalkyl, halo-alkyl (such as trifluoromethyl) and arylalkyl), aryl, alkoxy (including arylalkoxy), aryloxy, alkylthio, alkylsulfoxyl and alkylsulfonyl.

Preferably, the compounds of formula (I) are selected from compounds in which $R_4$ is selected from hydrogen and alkyl, preferably from hydrogen and lower alkyl. Where $R_4$ is lower alkyl, $R_4$ is preferably methyl or ethyl.

Preferably, the compounds of formula (I) are selected from compounds in which $R_5$ is hydrogen.

Preferably, the compounds of formula (I) are selected from compounds in which $R_6$ is selected from halogen (preferably fluoro and chloro) and hydrogen.

Preferably, the compounds of formula (I) are selected from compounds in which only one of $X_1$, $X_2$, $X_3$ and $X_4$ is nitrogen. It is preferred that $X_1$ is C—$R_7$. Where only one of $X_1$, $X_2$, $X_3$ and $X_4$ is nitrogen, preferably $X_2$, $X_3$ or $X_4$ is nitrogen, more preferably $X_2$ or $X_4$ is nitrogen and most preferably $X_2$ is nitrogen. Where two or more of $X_1$, $X_2$, $X_3$ and $X_4$ are nitrogen, it is preferred that at least $X_2$, preferably $X_2$ and $X_4$, are nitrogen.

It is preferred that one or more or all of $R_7$ to $R_{10}$ are hydrogen.

In a preferred embodiment, the compounds of formula (I) are selected from 1-(1H-pyrrolo[2,3-f]quinolin-1-yl)-2-propylamine, 1-(1H-pyrrolo[3,2-h]isoquinolin-1-yl-2-propylamine, 1-(5-chloro-1H-pyrrolo[2,3-f]quinolin-1-yl)-2-propylamine and 1-(1H-pyrrolo[2,3-f]isoquinolin-1-yl)-2-propylamine, and preferably the (S)-enantiomers thereof. 1-(1H-Pyrrolo[3,2-h]isoquinolin-1-yl)-2-propylamine is particularly preferred. Where the compounds of formula (I) are in salt form, the fumarate salt is preferred.

The compounds of the invention may contain one or more asymmetric carbon atoms, so that the compounds can exist in different stereoisomeric forms. The compounds can be, for example, racemates or optically active forms. The optically active forms can be obtained by resolution of the racemates or by asymmetric synthesis.

In a preferred embodiment of the invention, a compound of formula (I) is in the form of its (S)-enantiomer, substantially free of its (R)-enantiomer. As used herein, the term "substantially free of its (R)-enantiomer" means that a composition comprising a compound of formula (I) contains a greater proportion of the (S)-enantiomer of the compound of formula (I) in relation to the (R)-enantiomer of the compound of formula (I). In a preferred embodiment of the present invention, the term "substantially free of its (R)-enantiomer", as used herein, means that the composition contains at least 90% by weight of the (S)-enantiomer and 10% by weight or less of the (R)-enantiomer. In a further preferred embodiment, the term "substantially free of its (R)-enantiomer" means that the composition contains at least 99% by weight of the (S)-enantiomer and 1% or less of the (R)-enantiomer. In another preferred embodiment, the term "substantially free of its (R)-enantiomer" means that the composition contains 100% by weight of the (S)-enantiomer. The above percentages are based on the total amount of a compound of formula (I) present in the composition.

According to a further aspect of the invention, there is provided a compound of formula (I) for use in therapy.

The compounds of formula (I) may be used in the treatment (including prophylactic treatment) of disorders associated with 5-HT$_2$ receptor function. The compounds may act as receptor agonists or antagonists. Preferably, the compounds may be used in the treatment (including prophylactic treatment) of disorders associated with 5-HT$_{2B}$ and/or 5-HT$_{2C}$ receptor function. Preferably, the compounds may be used in the treatment (including prophylactic treatment) of disorders where a 5-HT$_{2C}$ receptor agonist is required.

The compounds of formula (I) may be used in the treatment or prevention of central nervous disorders such as depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioural disorders, behavioural disorders associated with dementia, organic mental disorders, mental disorders in childhood, aggressivity, age-related memory disorders, chronic fatigue syndrome, drug and alcohol addiction, obesity, bulimia, anorexia nervosa or premenstrual tension; damage of the central nervous system such as by trauma, stroke, neurodegenerative diseases or toxic or infective CNS diseases such as encephalitis or meningitis; cardiovascular disorders such as thrombosis; gastrointestinal disorders such as dysfunction of gastrointestinal motility; diabetes insipidus; and sleep apnea.

According to a further aspect of the invention, there is provided use of a compound of formula (I) in the manufacture of a medicament for the treatment including prophylaxis) of the above-mentioned disorders. In a preferred embodiment, here is provided use of a compound of formula (I) in the manufacture of a medicament for the treatment (including prophylaxis) of obesity.

According to a further aspect of the invention, there is provided a method of treatment (including prophylaxis) of a disorder selected from the group consisting of the above-mentioned disorders comprising administering to a patient in need of such treatment an effective dose of a compound of formula (I). In a preferred embodiment, there is provided a method of treatment (including prophylaxis) of obesity.

According to a further aspect of the invention, there is provided a pharmaceutical composition comprising a compound of formula (I) in combination with a pharmaceutically acceptable carrier or excipient and a method of making such a composition comprising combining a compound of formula (I) with a pharmaceutically acceptable carrier or excipient.

According to a further aspect of the invention, there is provided a method of preparing a compound of formula (I).

Compounds of the invention may be prepared according to Reaction Scheme 1 below. $R_1$ to $R_6$ and $X_1$ to $X_4$ are as previously defined. The pyrroloquinolinyl-alkylethanol (III) may be formed by reaction of the pyrroloquinoline (II) with an alkylene oxide in the presence of a strong base such as sodium hydride. The corresponding azido derivative (V) can be formed in a two step procedure from the derivative (III) by formation of the mesylate (IV), obtained by reaction of (III) with methanesulfonyl chloride in the presence of a base such as triethylamine, and subsequent treatment of the mesylate (IV) with sodium azide in a solvent such as dimethyl formamide. The pyrroloquinoline (I) ($R_1$=$R_2$=H) can then be obtained by reduction of the azide (V) via catalytic hydrogenation in the presence of a catalyst such as platinum oxide.

Reaction Scheme 1

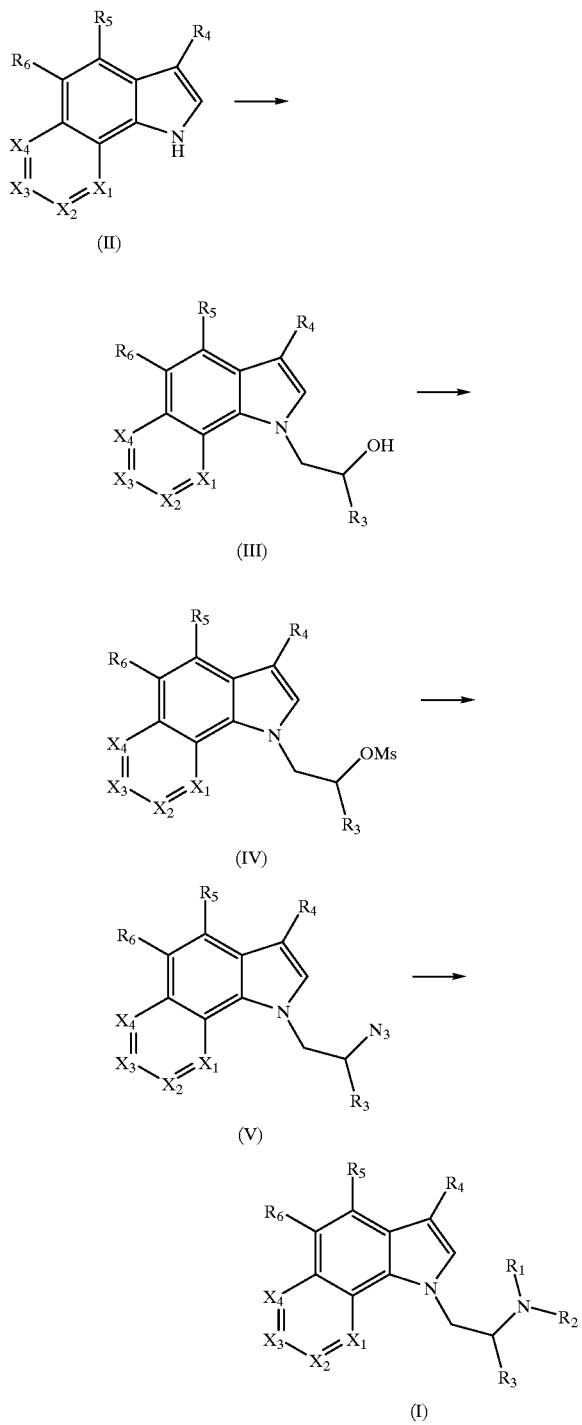

(II)

(III)

(IV)

(V)

(I)

Alternatively compounds of the invention may be prepared according to Reaction Scheme 2 below. The carbamate (VI) may be formed by reaction of the pyrroloquinoline (II) with a carbamylethylsulfonate in the presence of a strong base such as potassium hydroxide in a solvent such as methyl sulfoxide. The pyrroloquinoline (I) ($R_1$=$R_2$=H) may be obtained by reaction of the carbamate (VI) with a reagent suitable to reveal the protected amine function.

Reaction Scheme 2

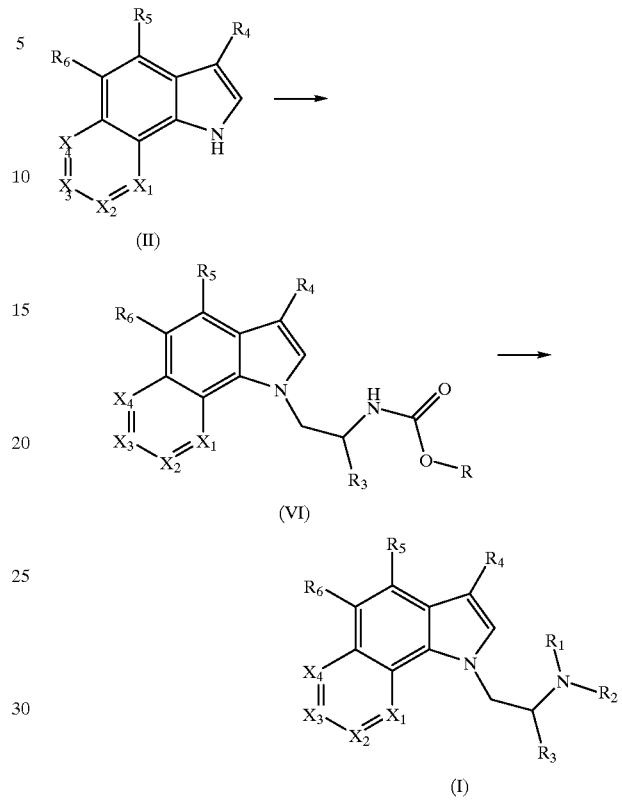

(II)

(VI)

(I)

The compounds of formula (I) ($R_1$ and/or $R_2$=alkyl) may be prepared from compounds of formula (I) ($R_1$ $R_2$=H) by standard methods such as reductive alkylation with an appropriate aldehyde or ketone in the presence of a reducing agent such as sodium triacetoxyborohydride, formic acid or sodium cyanoborohydride.

If, in any of the processes mentioned herein, any of the substituent groups $R_4$ to $R_{10}$ is other than the one required, the substituent group may be converted to the desired substituent by known methods. The substituents $R_4$ to $R_{10}$ may also need protecting against the conditions under which the reaction is carried out. In such a case, the protecting group may be removed after the reaction has been completed.

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base, an acid addition salt, particularly a pharmaceutically acceptable acid addition salt, may be obtained by dissolving the free base in a suitable organic solvent and treating the solution with an acid, in accordance with conventional procedures for preparing acid addition salts from basic compounds.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) transdermal or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropylmethylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulating agents such as suspending, stabilizing and/or dispersing agents.

Alternatively, the active ingredient may be in powder form for reconstitution with a suitable vehicle, e.g. sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., obesity) is 0.1 to 500 mg of the active ingredient per unit dose which could be administered, for example, 1 to 4 times per day.

The invention will now be described in detail with reference to the following examples. It will be appreciated that the invention is described by way of example only and modification of detail may be made without departing from the scope of the invention.

EXPERIMENTAL

Assay Procedures

1. Binding to Serotonin Receptors

The binding of compounds of formula (I) to serotonin receptors was determined in vitro by standard methods. The preparations were investigated in accordance with the assays given hereinafter.

Method (a): For the binding to the $5\text{-}HT_{2C}$ receptor the $5\text{-}HT_{2C}$ receptors were radiolabeled with $[^3H]\text{-}5\text{-}HT$. The affinity of the compounds for $5\text{-}HT_{2C}$ receptors in a CHO cell line was determined according to the procedure of D. Hoyer, G. Engel and H. O. Kalkman, *European J. Pharmacol.*, 1985, 118,13–23.

Method (b): For the binding to the $5\text{-}HT_{2B}$ receptor the $5\text{-}HT_{2B}$ receptors were radiolabeled with $[^3H]\text{-}5\text{-}HT$. The affinity of the compounds for human $5\text{-}HT_{2B}$ receptors in a CHO cell line was determined according to the procedure of K. Schmuck, C. Ullmer, P. Engels and H. Lubbert, *FEBS Lett.*, 1994, 342, 85–90.

Method (c): For the binding to the $5\text{-}HT_{2A}$ receptor the $5\text{-}HT_{2A}$ receptors were radiolabeled with $[^{125}I]\text{-}DOI$. The affinity of the compounds for $5\text{-}HT_{2A}$ receptors in a CHO cell line was determined according to the procedure of D. J. McKenna and S. J. Peroutka, *J. Neurosci.*, 1989, 9, 3482–90.

The thus determined activity of compounds of formula (I) is shown in Table 1.

TABLE 1

| Compound | $K_i$ (2C) | $K_i$ (2B) | $K_i$ (2A) |
| --- | --- | --- | --- |
| Example 1 | 9 nM | 12 nM | 45 nM |
| Example 2 | 22 nM | 5 nM | 37 nM |
| Example 3 | 24 nM | 9 nM | 40 nM |
| Example 4 | 156 nM | 84 nM | 173 nM |
| Example 8 | 45 nM | 88 nM | 90 nM |

2. Functional Activity

The functional activity of compounds of formula (I) was assayed using a Fluorimetric Imaging Plate reader (FLIPR). CHO cells expressing the human $5\text{-}HT_{2C}$ or human $5\text{-}HT_{2A}$ receptors were counted and plated into standard 96 well microtitre plates on the day before testing to give a confluent monolayer. The cells were then dye loaded with the calcium sensitive dye, Fluo-3-AM. Unincorporated dye was removed using an automated cell washer to leave a total volume of 100 µL/well of assay buffer (Hanks balanced salt solution containing 20 mM Hepes and 2.5 mM probenecid). The drug (dissolved in 50 µL of the assay buffer) was added at a rate of 70 µL/sec to each well of the FLIPR 96 well plate during fluorescence measurements. The measurements were taken at 1 sec intervals and the maximum fluorescent signal was measured (approx 10–15 secs after drug addition) and compared with the response produced by 10 µM 5-HT (defined as 100%) to which it was expressed as a percentage response (relative efficacy). Dose response curves were constructed using Graphpad Prism (Graph Software Inc.).

The thus determined activity of compounds of formula (I) is shown in Table 2.

TABLE 2

| Compound | $h5\text{-}HT_{2A}$ $EC_{50}$ (nM) | Relative Efficacy (%) | $h5\text{-}HT_{2C}$ $EC_{50}$ (nM) | Relative Efficacy (%) |
| --- | --- | --- | --- | --- |
| Example 1 | 360 | 100 | 12 | 93 |
| Example 2 | 87 | 96 | 7 | 85 |
| Example 4 | 870 | 54 | 142 | 89 |

TABLE 2-continued

| Compound | h5-HT$_{2A}$ EC$_{50}$ (nM) | Relative Efficacy (%) | h5-HT$_{2C}$ EC$_{50}$ (nM) | Relative Efficacy (%) |
|---|---|---|---|---|
| Example 5 | 52 | 80 | 5 | 86 |
| Example 7 | 636 | 61 | 36 | 83 |
| Example 8 | 1066 | 31 | 99 | 24 |
| Example 9 | 1301 | 65 | 85 | 90 |

3. In Vivo Efficacy

The in vivo efficacy of 5-HT$_{2C}$ agonists was assessed by the ability of the compounds to induce three specific behaviours (5HT$_{2C}$ Syndrome) in rats.

The 5-HT$_{2C}$ syndrome is a rapid screening method to assess the in vivo efficacy of 5-HT$_{2C}$ agonists through their ability to induce three specific behaviours in rats. The animals were dosed with either a positive control (mCPP), test compound or vehicle, either s.c. or p.o.. The animals were observed on an open bench, typically 30, 60 and 180 minutes after dosing and the degree of syndrome was assessed over a two minute period on a scale of 0–3 depending on the presence and severity of splayed limbs, hunched posture and retro-pulsion, the three specific behaviours which constitute the syndrome. Data were analysed using Kruskal-Wallis Analysis of Variance followed with appropriate post-hoc tests. All statistical analysis were conducted using Excel version 7.0 (Microsoft Corp.) and Statistica version 5.0 (Statsoft, Inc.).

The thus determined activities of Examples 1 and 2 indicate that after a dose of 10 mg/kg s.c. the compounds maintain significant pharmacological efficacy for at least 180 minutes.

4. Regulation of Feeding Behaviour

The in vivo activity of compounds of formula (I) on feeding behaviour was assayed by measuring food consumption in food deprived animals.

Test compounds were assessed following acute administration. Each study utilised a between-subjects design (typically n=8) and compared the effects of doses of the test agent to those of vehicle and a positive control.

The anorectic drug d-fenfluramine normally serves as a positive control. The route of drug administration, drug volume and injection-test-interval are dependent upon the compounds used. A palatable wet mash, made by adding powdered lab chow and water in a ratio of 1:2 and mixing to a smooth consistency, was presented in 120 ML glass jars for 60 minutes each day. Intake was measured by weighing before and after each session. Care was taken to collect all spillage. Animals were allowed to habituate to the wet mash meal for 10 days. After drug administration, animals were allowed to consume the wet mash. Food consumption was assayed at pre-determined time points (typically 1, 2 and 4 hours after administration). Food intake data were subjected to one-way analysis of variance (ANOVA) with drug as a between-subjects factor. A significant main effect was followed up by the performance of Dunnett's test in order to assess which treatment mean(s) were significantly different from the control mean. All statistical analyses were performed using Statistica Software, Version 5.0 (Statsoft Inc.) and Microsoft Excel 7.0 (Microsoft Corp.).

The thus determined activities of Examples 1 and 2 indicate that the compounds maintain significant hypophagia 2 hours after a dose of 10 mg/kg s.c.

Synthetic Examples

Example 1

(S)-1-(1H-Pyrrolo[2,3-f]quinolin-1-yl)-2-propylamine

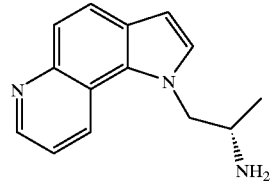

(R)-1-(1H-Pyrrolo[2,3-f]quinolin-1-yl)-2-propanol

A mixture of sodium hydride, 60% dispersion in mineral oil, (0.76 g, 18.5 mmol) and THF (30 mL) was cooled to 0° C. under Ar. A mixture of 1H-pyrrolo[2,3-f]quinoline (G. Bartoli, G. Palmieri, M. Bosco and R. Dalpozzo, *Tetrahedron Letts.*, 1989, 30, 2129–2132) (2.5 g, 14.8 mmol) and THF (20 mL) was added and the mixture was left at 0° C. for 1 h. (R)-propylene oxide (2.1 mL, 30 mmol) was added and the mixture was left at room temperature for 48 h. Saturated ammonium chloride solution (100 mL) was added and the mixture was extracted with Et$_2$O (3×100 mL), the extracts were combined, washed with brine (2×100 mL), dried (MgSO$_4$), concentrated in vacuo and purified by column chromatography [SiO$_2$; Et$_2$O] to give the product (0.61 g, 18% yield) as a pale yellow oil: IRv$_{max}$(Nujol)/cm$^{-1}$ 3106, 1361, 1117, 826, 805, and 731; NMR δ$_H$ (400 MHz, CDCl$_3$) 1.35 (3H, d, J 6.5 Hz), 2.76 (1H, br), 4.33 (1H, m), 4.44 (1H, m), 4.56 (I1H, m), 6.64 (1H, d, J 3.0 Hz), 7.20 (1H, d, J 3.0 Hz), 7.30 (1H, dd, J8.5 and 4.5 Hz), 7.71 (1H, d, J 9.0 Hz), 7.87 (1H, d, J 9.0 Hz), 8.52 (1H, d, J 8.5 Hz) and 8.67 (1H, m).

(S)-1-(2-Azidopropyl)-1H-pyrrolo[2,3-f]quinoline

A mixture of (R)-1-(1H-pyrrolo[2,3-f]quinolin-1-yl)-2-propanol (0.58 g, 2.6 mmol), CH$_2$Cl$_2$ (10 mL) and triethylamine (0.4 mL, 2.8 mmol) was cooled to 0° C. Methanesulfonyl chloride (0.2 mL, 2.8 mmol) was added and the yellow mixture was left at room temperature for 1 h. Brine (50 mL) was added and the mixture was extracted with CH$_2$Cl$_2$ (3×50 mL). The extracts were combined, washed with brine (50 mL), dried (MgSO$_4$) and concentrated in vacuo to give a pale yellow solid (0.76 g), which was added to a mixture of DMF (10 mL) and sodium azide (0.3 g, 4.8 mmol). The mixture was heated at 70° C. for 16 h. Brine (50 mL) was added and the mixture was extracted with Et$_2$O (3×50 mL), the extracts were combined, washed with brine (50 mL), dried (MgSO$_4$), concentrated in vacuo and purified by column chromatography [SiO$_2$; EtOAc-hexane (1:1)] to give the product (0.32 g, 53% yield) as a pale yellow oil: IRv$_{max}$ (liquid film)/cm$^{-1}$ 2119, 1356, 1259, 826, 807, 734, and 696; NMR δ$_H$ (400 MHz, CDCl$_3$) 1.37 (3H, d, J 6.5 Hz), 4.0 (1H, m), 4.50 (2H, m), 6.70 (1H, d, J 3.0 Hz), 7.17 (1H, d, J 3.0 Hz), 7.46 (1H, dd, J 8.5 and 4.5 Hz), 7.80 (1H, d, J 9.0 Hz), 7.94 (1H, J 8.5 Hz), 8.47 (1H, d, J 8.5 Hz) and 8.85 (1H, d, J 4.5 Hz).

(S)-1-(1H-Pyrrolo[2,3-f]quinolin-1-yl)]-2-propylamine hydrochloride

A mixture of (S)-1-(2-azidopropyl)-1H-pyrrolo[2,3-f] quinoline (0.45 g, 1.8 mmol), EtOH (10 mL) and platinum (IV)oxide (0.02 g, 0.09 mmol) was stirred under H$_2$ for 12 h. The mixture was filtered through Celite® and the solid washed with Et$_2$O (50 mL). The filtrate was concentrated in vacuo to give a pale yellow oil, which was taken up in Et$_2$O (5 mL) and cooled to 0° C. A solution of HCl in ether (1.0 M, 1.8 mL, 1.8 mmol) was added dropwise and the mixture was left to stir at room temperature for 10 min. The mixture was concentrated in vacuo and recrystallised (2-propanol) to give the product (0.46 g, 97%) as an orange solid: NMR $\delta_H$ (400 MHz, d$_6$DMSO) 1.16 (3H, d, J 6.5 Hz), 3.70 (1H, m), 4.72 (1H, dd, J 15 and 8.5 Hz), 5.10 (1H, d, J 15 and 6.0 Hz 6.82 (1H, d, J 3.0 Hz), 7.65 (1H, d, J 3.0 Hz), 7.76 (1H, dd, J 8.0 and 4.5 Hz), 7.82 (1H, d, J 8.5 Hz), 8.13 (1H, d, J 8.5 Hz), and 8.48 (3H, br), 8.95 (1H, d, J 4.5 Hz) and 9.23 (1H, d, J 8.0 Hz).

(S)-1-(1H-Pyrrolo[2,3-f]quinolin-1-yl)-2-propylamine fumarate

A solution of (S)-1-[1-(1H-pyrrolo[2,3-f]quinolinyl)]-2-propylamine hydrochloride (0.047 g, 0.18 mmol) in water (2 mL) was treated with a solution of NaOH (2 N, 2 mL) and the mixture was extracted with ethyl acetate (2×5 mL). The combined extracts were dried (MgSO$_4$), filtered and concentrated in vacuo to give (S)-1-(1H-pyrrolo[2,3-f]quinolin-1-yl)]-2-propylamine as a yellow oil (0.04 g). The oil was dissolved in 2-propanol (5 mL) and boiled at reflux while fumaric acid (0.02 g, 0.18 mmol) was added. On cooling, the crystallised product was filtered and dried in vacuo to give (S)-1-(1H-pyrrolo[2,3-f]quinolin-1-yl)-2-propylamine fumarate as a yellow solid (0.047 g, 77%), m.p. 222–224° C. Found: C, 63.24; H, 5.74; N, 11.99%. $C_{14}H_{15}N_3 \cdot C_4H_4O_4$ requires: C, 63.33; H, 5.61; N, 12.30%.

Example 2

(R)-1-(1H-Pyrrolo[2,3-f]quinolin-1-yl)-2-propylamine

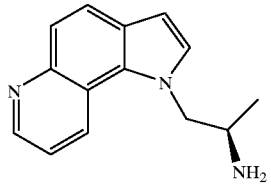

(S)-1-(1H-pyrrolo [2,3-f]quinolin-1-yl)-2-propanol (S)-1-(1H-Pyrrolo[2,3-f]quinolin-1-yl)-2-propanol was prepared according to the method described in Example 1 using 1H-pyrrolo[2,3-f]quinoline and (S)-propylene oxide to produce 0.36 g (17% yield) of the product as a pale yellow oil: IRv$_{max}$ (Nujol)/cm$^{-1}$ 3106, 1361, 1117, 826, 805 and 731; NMR $\delta_H$ (400 MHz, CDCl$_3$) 1.36 (3H, d, J 6.0 Hz), 2.75 (1H, br), 4.44 (2H, m), 4.56 (1H, m), 6.63 (1H, d, J 3.0 Hz), 7.19 (1H, d, J 3.0 Hz), 7.30 (1H, dd, J 8.5 and 4.0 Hz), 7.70 (1H, d, J 8.5 Hz), 7.86 (1H, d, J 9.0 Hz), 8.53 (1H, d, J 9.0 Hz) and 8.66 (1H, d, J 4.0 Hz).

(R)-1-(2-Azidopropyl)-1H-pyrrolo[2,3-f]quinoline (R)-1-(2-Azidopropyl)-1H-pyrrolo[2,3-f]quinoline was prepared according to the method described in Example 1 using (S)-1-(1H-pyrrolo[2,3-f]quinolin-1-yl)-2-propanol to produce 0.23 g (72% yield) of the product as a pale yellow oil: IRv$_{max}$ (liquid film)/cm$^{-1}$ 2118, 1356, 1294, 1259, 826 and 807; NMR $\delta_H$ (400 MHz, CDCl$_3$) 1.37 (3H, d, J 6.5 Hz), 4.06 (1H, m), 4.50 (2H, m), 6.70 (1H, d, J 3.0 Hz), 7.17 (1H, d, J 3.0 Hz), 7.45 (1H, dd, J 8.5 and 4.0 Hz), 7.81 (1H, d, J 8.5 Hz), 7.94 (1H, d, J 8.5 Hz), 8.48 (1H, d, J 8.5 Hz) and 8.85 (1H, d, J 4.0 Hz).

(R)-1-(1H-Pyrrolo[2,3-f]quinolin-1-yl)-2-propylamine hydrochloride (R)-1-(1H-Pyrrolo[2,3-f]quinolin-1-yl)-2-propylamine hydrochloride was prepared according to the method described in Example 1 using (R)-1-(2-azidopropyl)-1H-pyrrolo[2,3-f]quinoline to produce 0.20 g (95% yield) of the product as an orange solid: IRv$_{max}$(Nujol)/cm$^{-1}$ 2725, 2570, 1354, 1302, 823 and 723; NMR $\delta_H$ (400 MHz, d$_6$DMSO) 1.15(3H, d, J 6.5 Hz), 3.68 (1H, m), 4.70 (1H, m),5.04 (1H, m), 6.77 (1H, d, J 3.0 Hz), 7.58 (1H, d, J 3.0 Hz), 7.68 (1H, dd, J 8.5 and 4.5 Hz), 7.74 (1H, d, J 8.0 Hz), 8.04 (1H, d, J 8.5 Hz), 8.40 (3H, br), 8.88 (1H, d, J 4.5 Hz) and 9.04 (1H, d, J 8.0 Hz).

(R)-1-(1H-Pyrrolo[2,3f]quinolin-1propylamine fumarate (R)-1-(1H-Pyrrolo[2,3-f]quinolin-1-yl)-2-propylamine fumarate was prepared from (R)-1-(1H-Pyrrolo[2,3-f]quinolin-1-yl)-2-propylamine hydrochloride according to the method described in Example 1 to give 0.030 g (68%) of the product as a yellow solid: mp 223–5° C.; Found: C, 62.50; H, 5.61; N, 11.91%. $C_{14}H_{15}N_3 \cdot C_4H_4O_4 \cdot 0.25\ h_2O$ requires: C, 62.51; H, 5.68; N, 12.15%.

Example 3

(RS)-1-(1H-Pyrrolo[2,3-f]quinolin-1-yl)-2-propylamine hydrochloride

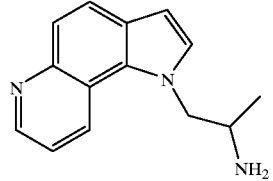

(RS)-1-(1H-Pyrrolo[2,3-f]quinolin-1-yl)]-2-propanol (RS)-1-(1H-Pyrrolo[2,3-f]quinolin-1-yl)]-2-propanol was prepared according to the method described in Example 1 using 1H-pyrrolo[2,3-f]quinoline and (RS)-propylene oxide to produce 0.22 g (69% yield) of the product as a pale yellow oil: IRv$_{max}$ (Nujol)/cm$^{-1}$ 3107, 1360, 1299, 1132, 827, 807 and 731; NMR $\delta_H$ (400 MHz, CDCl$_3$) 1.36 (3H, d, J 6 Hz), 4.44 (2H, m), 4.56 (1H, m), 6.64 (1H, d, J 3.0Hz), 7.20 (1H, d, J 3.0 Hz), 7.32 (1H, dd, J 8.5 and 4.0 Hz), 7.72 (1H, d, J 8.5 Hz), 7.87 (1H, d, J 8.5 Hz), 8.58 (1H, d, J 8.5 Hz) and 8.60 (1H, d, J 4.0 Hz).

(RS)-1-(2-Azidopropyl)-1H-pyrrolo[2,3-f]quinoline (RS)-1-(2-Azidopropyl)-1H-pyrrolo[2,3-f]quinoline was prepared according to the method described in Example 1 using (RS)-1-(1H-pyrrolo[2,3-f]quinolin-1-yl)-2-propanol to produce 0.12 g (68% yield) of the product as a pale yellow oil: IRv$_{max}$ (liquid film)/cm$^{-1}$ 2118, 1356, 1259, 826, 807, 734 and 696; NMR $\delta_H$ (400 MHz, CDCl$_3$) 1.33 (3H, d, J 6.5 Hz), 4.0 (1H, m), 4.45 (2H, m), 6.67 (1H, d, J 3.0 Hz), 7.13 (1H, d, J 3.0 Hz), 7.40 (1H, dd, J 9.0 and 4.0 Hz), 7.80 (1H, d, J 9.0 Hz), 7.92 (1H, d, J 8.0), 8.42 (1H, d,J8.5 Hz) and 8.82 (1H, d, J4.0 Hz).

(RS)-1-(1H-Pyrrolo[2,3-f]quinolin-1-yl)-2-propylamine hydrochloride (RS)-1-(1H-Pyrrolo[2,3-f]quinolin-1-yl)-2-propylamine hydrochloride was prepared according to the method described in Example 1 using (RS)-1-(2-azidopropyl)-1H-pyrrolo[2,3-f]quinoline to produce 0.06 g (95% yield) of the product as a pale yellow solid: NMR $\delta_H$ (400 MHz, d6DMSO) 1.16 (3H, d, J 6.5 Hz), 3.68 (1H, m), 4.71 (1H, dd, J 15 and 8.5 Hz), 5.07 (1H, dd, J 15 and 6.0Hz), 6.8 (1H, d, J 3.0Hz), 7.63 (1H, d, J3.0 Hz), 7.72 (1H, dd, J 8.5 and 4.5 Hz), 7.63 (1H, d, J 3.0 Hz), 8.1 (1H, d, J 8.5 Hz), 8.53 (3H, br), 8.91 (1H, d, J 4.5 Hz) and 9.17 (1H, d, J 8.0 Hz).

Example 4

(S)-1-(1H-Pyrrolo[2,3-f]isoquinolin-1-yl)-2-propylamine fumarate

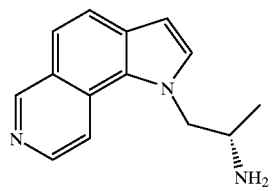

(R)-1-(1H-Pyrrolo[2,3-f]isoquinolin-1-yl)-2-propanol (R)-1-(1H-Pyrrolo[2,3-f]isoquinolin-1-yl)-2-propanol was prepared according to the method described in Example 1 using 1H-pyrrolo[2,3-f]isoquinoline (*Farmaco*, 1989, 44(12), 1141–55) and (R)-propylene oxide to give 0.77 g (71%) of the product as a white solid. A recrystallised sample [cyclohexane-ethanol (4:1)] gave mp 169–170° C.; Found: C, 74.09; H, 6.28; N, 12.27%. $C_{14}H_{14}N_2O$ requires C, 74.31; H, 6.24; N, 12.37%.

(S)-1-(2-Azidopropyl)-1H-pyrrolo[2,3-f]isoquinoline (S)-1-(2-Azidopropyl)-1H-pyrrolo[2,3-f]isoquinoline was prepared from (R)-1-(1H-Pyrrolo[2,3-f]isoquinolin-1-yl)-2-propanol according to the method described in Example 1 to give 0.33 g (99%) of the product as a yellow oil: IR $v_{max}$ (liquid film)/cm$^{-1}$ 3383, 2974, 2932, 2497 2119, 1733, 1674, 1615, 1501, 1376, 1334, 1225, 1094, 1058, 872, 822, 698 and 618; NMR $\delta_H$ (400 MHz, CDCl$_3$) 1.38 (3H, d, J 6.5 Hz) 4.09 (1H, m) 4.47 (1H, dd, J 8, 15 Hz) 4.60 (1H, dd, J 5.5, 15) 6.70 (1H, d, J 3 Hz) 7.20 (1H, d, J 3 Hz) 7.61 (1H, d, J 8.5 Hz) 7.82 (1H, d, J 8.5 Hz) 7.87 (1H, d, J 5.5 Hz) 8.58 (1H, s) 9.27 (1H, s).

(S)-1-(1H-Pyrrolo[2,3-f]isoquinolin-1-yl)-2-propylamine fumarate (S)-1-(1H-Pyrrolo[2,3-f]isoquinolin-1-yl)-2-propylamine fumarate was prepared from (S)-1-(2-azidopropyl)-1H-pyrrolo[2,3-f]isoquinoline according to the method described in Example 1 to give 0.095 g (21%) of the product as a white solid: mp 165° C.; Found: C, 59.31; H, 5.80; N, 10.41%. $C_{14}H_{15}N_3 \cdot 1.5C_4H_4O_4 \cdot 0.25H_2O$ requires C, 59.47; H, 5.37; N, 10.40%.

Example 5

(S)-1-(5-Chloro-1H-pyrrolo[2,3-f]-quinolin-1-yl)-2-propylamine fumarate

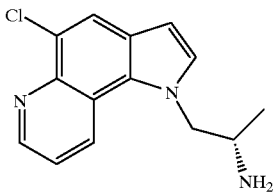

5-Chloro-1H-pyrrolo[2,3-f]quinoline

To a stirred solution of 8-chloro-5-nitroquinoline (5.0 g, 24 mmol) in tetrahydrofuran (70 mL) at −78° C. under Ar was added a solution of vinylmagnesium bromide (1.0 M in tetrahydrofuran, 72 mL, 72 mmol) over 5 min. The mixture was stirred for 40 minutes, poured into aqueous ammonium chloride solution (200 mL) and extracted with ether (3×100 mL). The combined organic extracts were washed (water, brine), dried (sodium sulfate), concentrated in vacuo and purified by column chromatography [SiO$_2$; ethyl acetate-heptane (1:1)] to give 5-chloro-1H-pyrrolo[2,3-f]quinoline as an orange solid (1.0 g, 21%): mp 248–250° C.; IR $v_{max}$ (Nujol)/cm$^{-1}$ 3198, 2924, 2854, 1500, 1465, 1377, 1364, 1290, 1162, 1126, 1085, 949, 887, 810, 780, 744, 706, 633, 599 and 512; NMR $\delta_H$ (400 Mz, CDCl$_3$) 6.64 (1H, d, J 3 Hz) 7.56 (1H, t, J 4 Hz) 7.65 (1H, dd, J2.5, 8.5 Hz) 8.14 (1H, s) 8.83 (1H, d, J 8.5 Hz) 8.88 (1H, d, J 2.5 Hz) 12.37 (1H, m).

(R)-1-(5-Chloro-1H-pyrrolo[2,3-f]quinolin-1-yl)-2-propanol (R)-1-(5-Chloro-1H-pyrrolo[2,3-f]quinolin-1-yl)-2-propanol was prepared from 5-chloro-1H-pyrrolo[2,3-f]quinoline according to the method described in Example 1 to give 0.27 g (21%) of the product as a clear oil which was used immediately.

(S)-1-(2-Azidopropyl)-5-chloro-1H-pyrrolo[2,3-f]quinoline (S)-1-(2-Azidopropyl)-5-chloro-1H-pyrrolo[2,3-f]quinoline was prepared according to the method described in Example 1 from (R)-1-(5-chloro-1H-pyrrolo[2,3-f]quinolin-1-yl)-2-propanol to give 0.066 g (23%) of the product as a clear oil which was used immediately.

(S)-1-(5-Chloro-1H-pyrrolo[2,3-f]-quinolin-1-yl)-2-propylamine fumarate

A solution of (S)-1-(2-azidopropyl)-5-chloro-1H-pyrrolo[2,3-f]quinoline (0.066 g, 0.2 mmol), triethylamine (0.06 mL), 1,3-propanedithiol (0.02 mL) and sodium borohydride (0.013 g, 0.34 mmol) in 2-propanol (5 mL) was stirred for 18 h. The mixture was partitioned between aqueous sodium hydroxide solution (2 M, 10 mL) and ether (3×10 mL). The combined organic extracts were washed (water, brine), dried (sodium sulfate), filtered through a pad of alumina and concentrated in vacuo to give an oil (0.041 g, 68%). The oil was dissolved in 2-propanol (0.5 mL) and added dropwise to a solution of fumaric acid (0.030 g, 0.26 mmol) in 2-propanol (5 mL) at 50° C. The solution was cooled to 0° C. and filtered. The filter-cake was washed (2-propanol, ether) and dried to give the product as a white solid (0.048 g, 55%): mp 228–229° C.; Found: C, 57.39; H, 4.90; N, 11.07%. $C_{14}H_{14}N_3Cl \cdot C_4H_4O_4$ requires C, 57.53; H, 4.83; N, 11.18%.

Example 6

(S)-1-(6-Methoxy-1H-pyrrolo[2,3-f]isoquinolin-1-yl)-2-propylamine fumarate

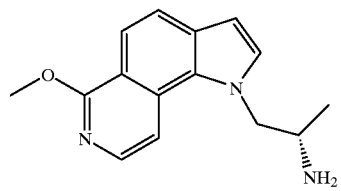

6-Methylisoquinoline-2-oxide

To a stirred solution of 6-methylisoquinoline (2.0 g, 14 mmol) in ether (80 mL) at 0° C. was added 3-chloroperbenzoic acid (57%, 4.3 g, 14 mmol). The mixture was warmed to room temperature, stirred for 3 h and filtered. The filter-cake was partitioned between chloroform (3×30 mL) and aqueous potassium carbonate solution (30 mL). The combined organic extracts were washed (brine), dried (sodium sulfate) and concentrated in vacuo to give the product as an off-white crystalline solid (1.2 g, 53%): mp 140–142° C.; IR $v_{max}$ (Nujol)/cm$^{-1}$ 3047, 2925, 2855, 1606, 1562, 1466, 1377, 1328, 1270, 1217, 1182, 1133, 984, 920, 878, 858, 823, 803, 766, 600, 500 and 498; NMR $\delta_H$ (400

MHz, CDCl₃) 2.53 (3H, s) 7.47 (1H, d, J 8.5 Hz) 7.59 (1H, d, J 7.5 Hz) 7.64 (1H, d, J 8.5 Hz) 8.11 (1H, dd, J 2,7.5 Hz) 8.73 (1H, s).

1-Chloro-6-methyl-5-nitroisoquinoline

To a stirred solution of 6-methylisoquinoline-2-oxide (0.95 g, 6.0 mmol) in chloroform (30 mL) was added phosphorus oxychloride (0.61 mL, 6.5 mmol). The mixture was heated to reflux for 2 h, cooled to room temperature, washed with aqueous sodium 15 hydrogen carbonate solution (3×20 mL), dried (sodium sulfate) and concentrated in vacuo to give an oil (1.0 g, 97%). The oil was dissolved in sulfuric acid (5 mL), cooled to 0° C. and treated with potassium nitrate (0.72 g, 7.1 mmol). The mixture was stirred for 2 h, poured into ice-water (50 mL) and filtered. The filter-cake was washed (water) and dried to give the product as a beige solid (1.36 g, 100%). A sample recrystallised from ethanol gave mp 171–173° C.; Found: C, 53.82; H, 3.19; N, 12.49%. C₁₀H₇N₂ClO₂ requires C, 53.95; H, 3.17; N, 12.58%.

1-Methoxy-6-methyl-5-nitroisoquinoline

A stirred solution of 1-chloro-6-methyl-5-nitroisoquinoline (1.2 g, 5.4 mmol) and sodium methoxide (0.6 g, 95%, 11 mmol) in methanol (20 mL) in a sealed-tube was heated to 80° C. for 2 h, cooled to room temperature and partitioned between ethyl acetate (3×30 mL) and water (50 mL). The combined organic extracts were washed (water, brine), dried (sodium sulfate) and concentrated in vacuo to give the product as a beige solid (0.87 g, 74%). A sample recrystallised from ethanol gave mp 94° C.; Found: C, 60.45; H, 4.58; N, 12.74%. C₁₁H₁₀N₂O₃ requires C, 60.55; H, 4.62; N, 12.83%.

6-Methoxy-1H-pyrrolo[2,3-f]isoquinoline

A stirred solution of 1-methoxy-6-methyl-5-nitroisoquinoline (0.82 g, 3.8 mmol), dimethylformamide dimethyl acetal (0.6 mL, 4.5 mmol) and pyrrolidine (0.4 mL, 4.8 mmol) in dimethyl formamide (10 mL) was heated to 100° C. for 3 h, cooled to room temperature and partitioned between water (50 mL) and ethyl acetate (3×30 mL). The combined organic extracts were washed (water, brine), dried (sodium sulfate) and concentrated in vacuo to give a dark red solid (1.18 g) which was dissolved in THF (2 mL) and added dropwise to a stirred suspension of Raney Nickel (0.5 g) in THF (20 mL) and methanol (10 mL). To the mixture was added dropwise hydrazine hydrate (2 mL) and the mixture was heated to 60° C. for 5 h, cooled to room temperature and filtered through a pad of kieselguhr. The filtrate was concentrated in vacuo and purified by column chromatography [SiO₂; ethyl acetate] to give 6-methoxy-1H-pyrrolo[2,3-f]isoquinoline as an orange solid (0.49 g, 65%). A recrystallised sample [cyclohexane-ethanol (10:1)] gave mp 166–168° C.; Found: C, 72.74; H, 5.10; N, 14.18%. C₁₂H₁₀N₂O requires C, 72.71; H, 5.08; N, 14.13%.

(S)-1-[2-(tert-Butoxycarbonylamino)propyl]-6-methoxy-1H-pyrrolo[2,3-f]isoquinoline A mixture of 6-methoxy-1H-pyrrolo[2,3-f]isoquinoline (0.40 g, 2.0 mmol) (S)-2-(tert-butoxycarbonylamino)propyl methanesulfonate (1.3 g, 5.1 mmol), powdered potassium hydroxide (85%, 0.40 g, 6.1 mmol) and methyl sulfoxide (10 mL) was heated to 38° C., stirred for 18 h, poured into ice-water (50 mL) and filtered. The filter-cake was washed (water) and dried to give the product as an off-white solid (0.54 g, 75%). A recrystallised sample [cyclohexane, ethanol (4:1)] gave mp 196–8° C.; Found: C, 67.04; H, 7.09; N, 11.66%. C₂₀H₂₅N₃O₃ requires C, 67.58; H, 7.09; N, 11.82%.

(S)-1-(6-Methoxy-1H-pyrrolo[2,3-f]isoquinolin-1-yl)-2-propylamine fumarate

A mixture (S)-2-(tert-butoxycarbonylamino)propyl-6-methoxy-1H-pyrrolo[2,3-f]isoquinoline (0.32 g, 0.9 mmol), conc. hydrochloric acid (0.3 mL) and methanol (5 mL) was heated to reflux for 3 h, cooled to room temperature and partitioned between dichloromethane (3×20 mL) and aqueous sodium hydroxide solution (2 M, 20 mL). The combined organic extracts were washed (water, brine), dried (sodium sulfate) and concentrated in vacuo to give a yellow oil (0.13 g) which was purified by column chromatography [Al₂O₃; ethyl acetate-methanol (20:1)] to give a clear oil (0.031 g). The oil was dissolved in 2-propanol (0.5 mL) and added to a solution of fumaric acid (0.02 g) in IPA (1 mL) at 50° C. The mixture was cooled to 0° C. and filtered. The filter-cake was washed (2-propanol, ether) and dried to give the product as a white, crystalline solid (0.037 g, 11%): mp 180–2° C.; Found: C, 60.64; H, 5.67; N, 10.87%. C₁₅H₁₇N₃O.1.2C₄H₄O₄ requires C, 60.27; H, 5.57; N, 10.65%.

Example 7

(S)-1-(1H-Pyrrolo[3,2-h]isoquinolin-1-yl)-2-propylamine fumarate

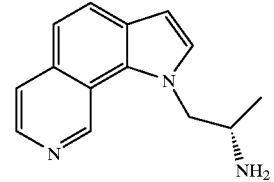

(S)-1-[2-(tert-Butoxycarbonylamino)propyl]-1H-pyrrolo[3,2-h]isoquinoline (S)-1-[2-(tert-Butoxycarbonylamino)propyl]-1H-pyrrolo[3,2-h]isoquinoline was prepared from 1H-pyrrolo[3,2-h]isoquinoline (*Indian J. Chem.*, 1971, 9(5), 402–3) according to the method described in Example 6 to give 0.35 g (43%) of the product as an oil; IR ν_{max} (Nujol)/cm⁻¹ 3368, 2957, 2925, 1746, 1680, 1531, 1501, 1459, 1357, 1254, 1177, 1061, 986, 841, 784, 746, 726, 695, 642 and 577; NMR δ_H (400 MHz, CDCl₃) 1.2 –1.5 (12H, m) 4.3 (1H, m) 4.5 (1H, m) 4.9 (1H, m) 6.67 (1H, d, J 3 Hz) 7.15 (1H, d, J 3 Hz) 7.45 (1H, d, J 8.5 Hz) 7.74 (1H, d, J 5.5 Hz) 7.89 (1H, d, J 8.5 Hz) 8.50 (1H, d, J 5.5 Hz).

(S)-1-(1H-Pyrrolo[3,2-h]isoquinolin-1-yl)-2-propylamine fumarate (S)-1-(1H-Pyrrolo[3,2-h]isoquinolinyl)-2-propylamine fumarate was prepared from (8)-2-( tert-Butoxycarbonylamino)propyl-1-(1H-pyrrolo[3,2-h]isoquinoline) according to the method described in Example 6 to give 0.22 g (7 1%) of the product as a white solid:

mp 153–4° C.; Found: C, 59.29; H, 5.72; N, 11.39%. C₁₄H₁₅N₃.C₄H₄O₄.1.25H₂O requires C, 59.41; H, 5.96; N, 11.55%.

Example 8

(S)-1-(1H-Pyrrolo[3,2-h]quinolin-1-yl)-2-propylamine hemifumarate

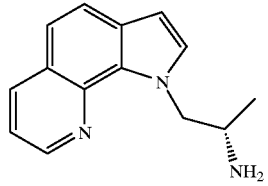

(S)-1-(1H-Pyrrolo[3,2-h]quinolinyl)-2-propylamine hemifumarate was prepared from 1H-pyrrolo[3,2-h]quinoline (*Farmaco*, 1992, 47(12), 1513–28) according to the method described in Example 6 to give 0.65 g (64%) of the product as a white solid: mp 212–4 C; Found: C, 67.40; H, 6.13; N, 14.57%. $C_{14}H_{15}N_3 \cdot 0.5C_4H_4O_4$ requires C, 67.83; H, 6.05; N, 14.83%.

Example 9

(S)-[1-(1H-Pyrrolo[2,3-f]quinolin-1-yl)-2-propyl]-(3,4-methylenedioxybenzyl)amine bis-fumarate

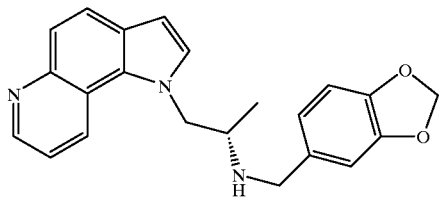

A mixture of (S)-1-(1H-pyrrolo[2,3-f]quinolin-1-yl)-2-propylamine (0.025 g, 0.11 mmol), 3,4-methylenedioxybenzaldehyde (0.033 g, 0.22 mmol) and methanol (1 mL) was shaken for 3 h. To the mixture was added Amberlite IRA-400 borohydride resin (2.5 mmol/g —$BH_4$, 0.12 g, 0.3 mmol) and the mixture was shaken for 18 h. To the mixture was added PS-benzaldehyde (2.5 mmol/g —CHO, 0.12 g, 0.3 mmol) and the mixture was shaken for 18 h and filtered. The filter-cake was washed with dichloromethane (2×1 mL) and methanol (2×1 mL) and the filtrate was concentrated in vacuo. The concentrate was dissolved in dichloromethane (2 mL) and Amberlyst-15 (0.5 g) was added. The mixture was shaken for 1 h and filtered. The filter-cake was washed with dichloromethane (2×1 mL) and methanol (2×1 mL), suspended in methanolic ammonia solution (2 M, 1 ML, 2 mmol), shaken for 1 h, and filtered. The filter-cake was washed (dichloromethane) and the filtrate was concentrated in vacuo, treated with a solution of fumaric acid (0.030 g, 0.26 mmol) in 2-propanol (2 mL), cooled to 0° C., shaken for 1 h and filtered. The filter-cake was dried to give the product as a beige solid (0.052 g, 79%): mp 171–175° C. (dec); NMR $\Delta_H$ (400 MHz, DMSO-$d_6$) 0.99 (3H, d, J 6.5 Hz) 3.15 (1H, m) 3.58 (1H, d, J 14 Hz) 3.73 (1H, d, J 14 Hz) 4.46 (1H, dd, J 8.5, 14.5 Hz) 4.76 (1H, dd, J 6, 14.5 Hz) 5.96 (2H, s) 6.66 (1H, d, J 7.5 Hz) 6.73 (1H, d, J 7.5 Hz) 6.87 (1H, s) 7.47 (1H, dd, J 4.5, 8.5 Hz) 7.50 (1H, d, J 3 Hz) 7.64 (1H, d, J 9 Hz) 7.94 (1H, d, J 9 Hz) 8.64 (1H, d, J 8.5 Hz) 8.77 (1H, d, J 4 Hz).

What is claimed is:

1. A chemical compound of formula (I):

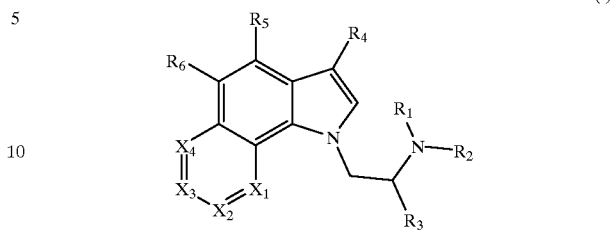

wherein:
$R_1$ to $R_3$ are independently selected from hydrogen and alkyl;
$R_4$ is selected from hydrogen, alkyl, alkoxy, formyl and cyano;
$X_1$ is selected from N and C—$R_7$;
$X_2$ is selected from N and C—$R_8$;
$X_3$ is selected from N and C—$R_9$;
$X_4$ is selected from N and C—$R_{10}$;
wherein at least one of $X_1$, $X_2$, $X_3$ and $X_4$ is N; and
$R_5$ to $R_{10}$ are independently selected from hydrogen, halogen, hydroxy, alkyl, aryl, alkoxy, aryloxy, alkylthio, arylthio, alkylsulfoxyl, alkylsulfonyl, arylsulfoxyl, arylsulfonyl, amino, monoalkylamino, dialkylamino, nitro, cyano, carboxaldehyde, alkylcarbonyl, arylcarbonyl, aminocarbonyl, monoalkylaminocarbonyl, dialkylaminocarbonyl, alkoxycarbonylamino, aminocarbonyloxy, monoalkylaminocarbonyloxy, dialkylaminocarbonyloxy, monoalkylaminocarbonylamino and dialkylaminocarbonylamino;
wherein said alkyl and aryl group(s) of $R_1$ to $R_{10}$ may be substituted or unsubstituted;
and pharmaceutically acceptable salts thereof.

2. A compound according to claim 1 wherein $R_1$ and $R_2$ are hydrogen.

3. A compound according to claim 1 wherein $R_1$ is hydrogen and $R_2$ is alkyl.

4. A compound according to claim 1 wherein $R_1$ is hydrogen and $R_2$ is methyl.

5. A compound according to claim 3, wherein $R_2$ is substituted by an aryl group.

6. A compound according to claim 5 wherein said aryl group is a substituted or unsubstituted phenyl or thienyl group.

7. A compound according to claim 1, wherein $R_3$ is alkyl.

8. A compound according to claim 1, where $R_3$ is methyl.

9. A compound according to claim 7, wherein the carbon atom to which $R_3$ is attached is in the (S)-configuration.

10. A compound according to claim 1 where $R_4$ is selected from hydrogen and alkyl.

11. A compound according to claim 1 wherein $R_5$ to $R_{10}$ are selected from hydrogen, halogen, hydroxy, alkyl, aryl, alkoxy, aryloxy, alkylthio, alkylsulfoxyl and alkylsulfonyl.

12. A compound according to claim 1 wherein $R_5$ is hydrogen.

13. A compound according to claim 1 wherein $R_6$ is hydrogen or halogen.

14. A compound according to claim 1, wherein any of $R_7$ to $R_{10}$ are hydrogen.

15. A compound according to claim 1 wherein only one of $X_1$, $X_2$, $X_3$ and $X_4$ is nitrogen.

16. A compound according to claim 1 wherein $X_2$ is nitrogen.

17. A compound according to claim 1 wherein $X_4$ is nitrogen.

18. A compound according to claim 1 wherein $X_1$ is C—$R_7$.

19. A compound according to claim 1 where the compounds of formula (I) are selected from the group consisting of 1-(1H-pyrrolo[2,3-f]quinolin-1-yl-2-propylamine, 1-(1H-pyrrolo[3,2-h]isoquinolin-1-yl)-2-propylamine, 1-(5-chloro-1H-pyrrolo[2,3-f]quinolin-1-yl)-2-propylamine and 1-(1H-pyrrolo[2,3-f]isoquinolin-1-yl)-2-propylamine.

20. A compound according to claim 1 which is the (S)-enantiomer thereof.

21. A method of treatment of disorders of the central nervous system; damage to the central nervous system; cardiovascular disorders; gastrointestinal disorders; diabetes insipidus, and sleep apnea, comprising administering to a patient in need of such treatment an effective dose of a compound of formula (I) as set out in claim 1.

22. A method according to claim 21, wherein the disorders of the central nervous system are selected from the group consisting of depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioural disorders, behavioural disorders associated with dementia, organic mental disorders, mental disorders in childhood, aggressivity, age-related memory disorders, chronic fatigue syndrome, drug and alcohol addition, obesity, bulimia, anorexia nervosa and premenstrual tension.

23. A method according to claim 21 wherein the damage to the central nervous system is by trauma, stroke, neurodegenerative diseases or toxic or infective CNS diseases.

24. A method according to claim 23 wherein said toxic or infective CNS disease is encephalitis or meningitis.

25. A method according to claim 21 wherein the cardiovascular disorder is thrombosis.

26. A method according to claim 21 wherein the gastrointestinal disorder is dysfunction of gastrointestinal motility.

27. A method according to claim 21 wherein said disorder of the central nervous system is obesity.

28. A method according to claim 21 wherein said treatment is prophylactic treatment.

29. A pharmaceutical composition comprising a compound of formula (I) as set out in claim 1, in combination with a pharmaceutically acceptable carrier or excipient.

* * * * *